United States Patent
Li

(10) Patent No.: US 9,254,159 B2
(45) Date of Patent: Feb. 9, 2016

(54) MEDICAL INSTRUMENTS FOR DIAPLASIS

(75) Inventor: Jiangming Li, Shijiazhuang (CN)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 1285 days.

(21) Appl. No.: 12/554,702

(22) Filed: Sep. 4, 2009

(65) Prior Publication Data

US 2011/0060376 A1 Mar. 10, 2011

(51) Int. Cl.
*A61F 2/46* (2006.01)
*A61B 17/88* (2006.01)

(52) U.S. Cl.
CPC .................................. *A61B 17/8866* (2013.01)

(58) Field of Classification Search
USPC ............. 606/86 R, 90, 96, 99, 101, 106, 100; 81/27; 173/90, 91, 118, 202; 254/19; 433/150, 151
See application file for complete search history.

(56) References Cited

U.S. PATENT DOCUMENTS

| | | | | |
|---|---|---|---|---|
| 2,337,971 A * | 12/1943 | Caviglia | | 433/151 |
| 2,437,014 A * | 3/1948 | Arnesen et al. | | 606/100 |
| 3,702,028 A * | 11/1972 | Edelman | | 433/150 |
| 4,476,861 A * | 10/1984 | Dimakos et al. | | 606/100 |
| 5,584,839 A * | 12/1996 | Gieringer | | 606/96 |
| 5,624,446 A * | 4/1997 | Harryman, II | | 606/96 |
| 5,690,640 A * | 11/1997 | Gotfried | | 606/105 |
| 6,349,618 B1 * | 2/2002 | Lowther | | 81/27 |
| 6,679,888 B2 * | 1/2004 | Green et al. | | 606/86 R |
| 6,936,052 B2 * | 8/2005 | Gellman et al. | | 606/99 |
| 6,976,988 B2 * | 12/2005 | Ralph et al. | | 606/99 |
| 7,578,824 B2 * | 8/2009 | Justin et al. | | 606/96 |
| 8,486,084 B2 * | 7/2013 | Huene | | 606/100 |
| 2003/0083668 A1 * | 5/2003 | Rogers et al. | | 606/100 |
| 2006/0178673 A1 * | 8/2006 | Curran | | 606/100 |
| 2008/0071282 A1 * | 3/2008 | Assell et al. | | 606/92 |
| 2008/0200984 A1 * | 8/2008 | Jodaitis | | A61F 2/442 623/17.16 |
| 2008/0208202 A1 * | 8/2008 | Williams | | 606/100 |
| 2009/0240256 A1 * | 9/2009 | Smith | | 606/100 |
| 2010/0256760 A1 * | 10/2010 | Hansell | | 623/17.11 |

FOREIGN PATENT DOCUMENTS

| | | |
|---|---|---|
| CN | 2512392 | 9/2002 |
| CN | 2643845 | 9/2004 |
| CN | 2717396 | 8/2005 |
| CN | 201150563 | 11/2008 |
| CN | 101361672 | 2/2009 |

* cited by examiner

*Primary Examiner* — Sameh Boles
(74) *Attorney, Agent, or Firm* — Maschoff Brennan

(57) ABSTRACT

A medical instrument includes a shaft and a movable element. The shaft has a first end having an engaging member. A second end of the shaft has a stopping member. The movable element is configured to move along the shaft. The medical instrument can be used to reduce a fracture. In use, this may include engaging a fractured bone segment with the engaging member and moving the movable element along the shaft towards the stopping member to create a force on the stopping member when the movable element comes in contact with the stopping member.

9 Claims, 6 Drawing Sheets

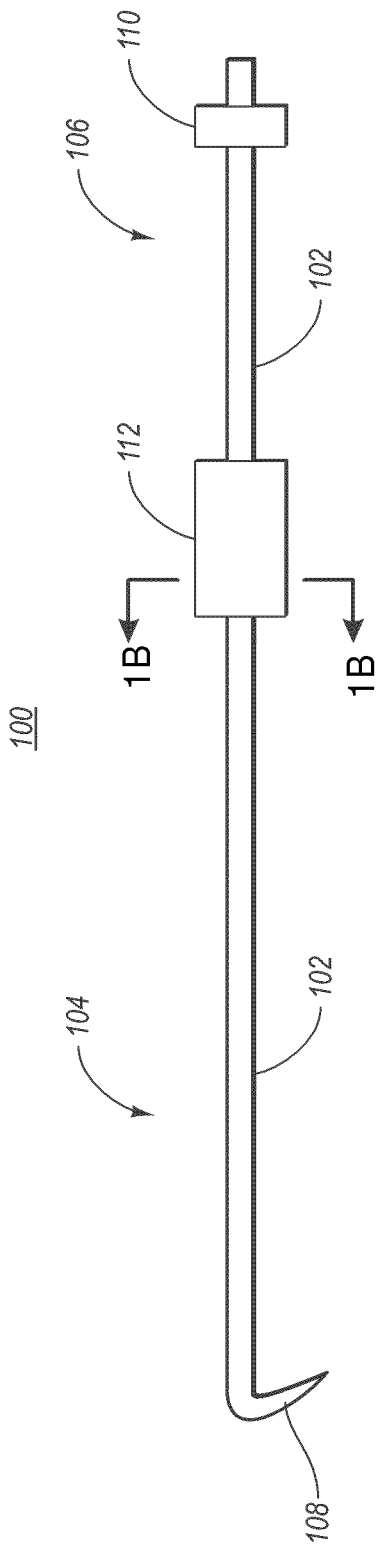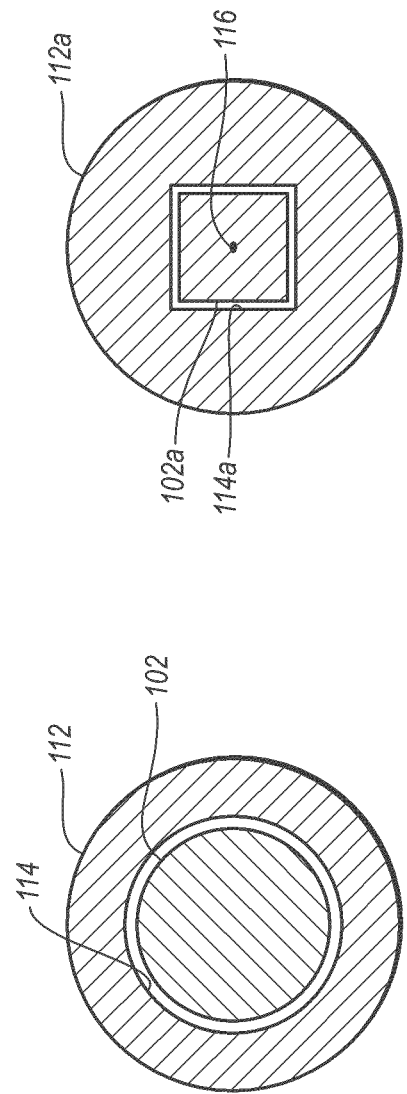
FIG. 1A
FIG. 1B
FIG. 1C

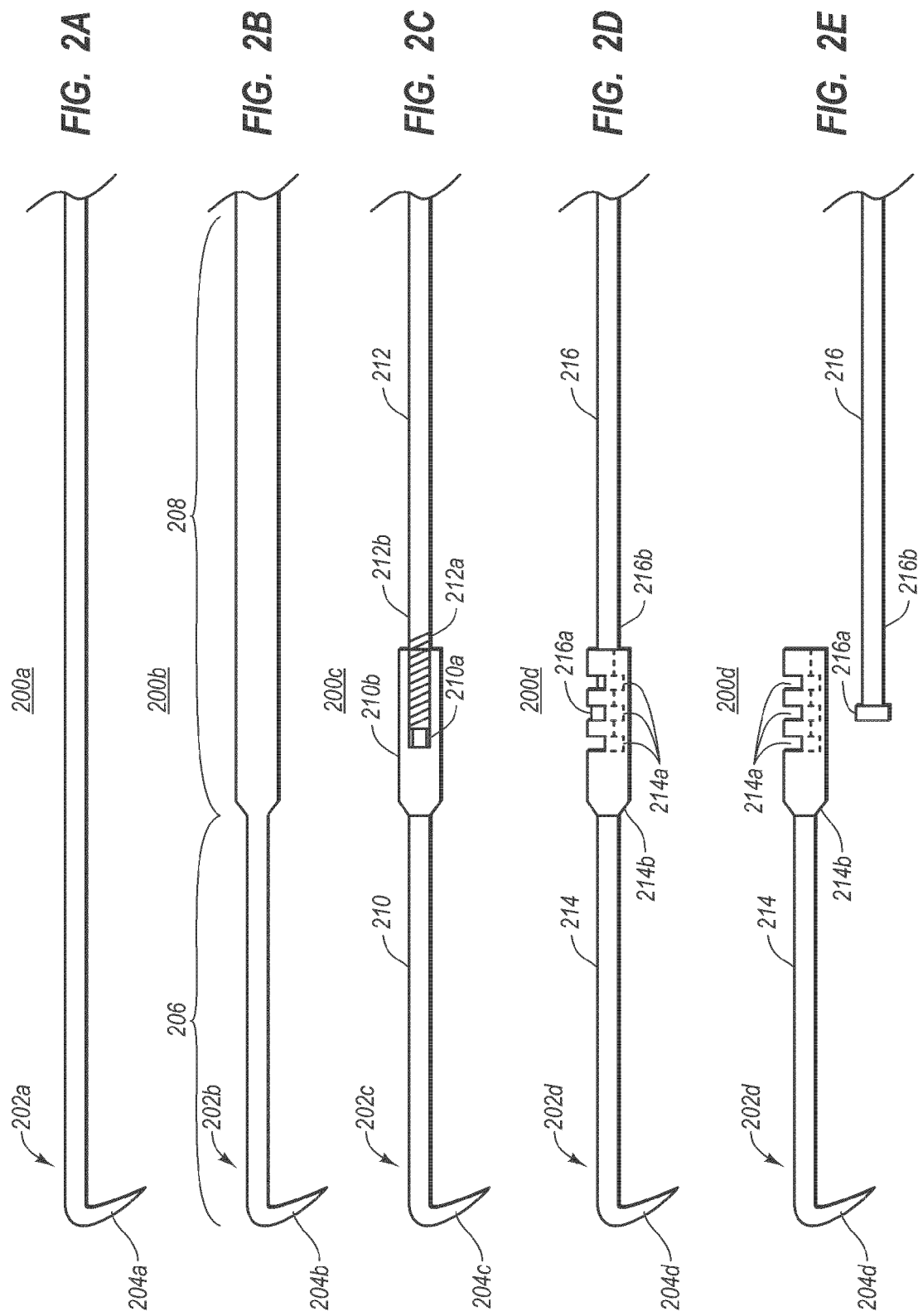

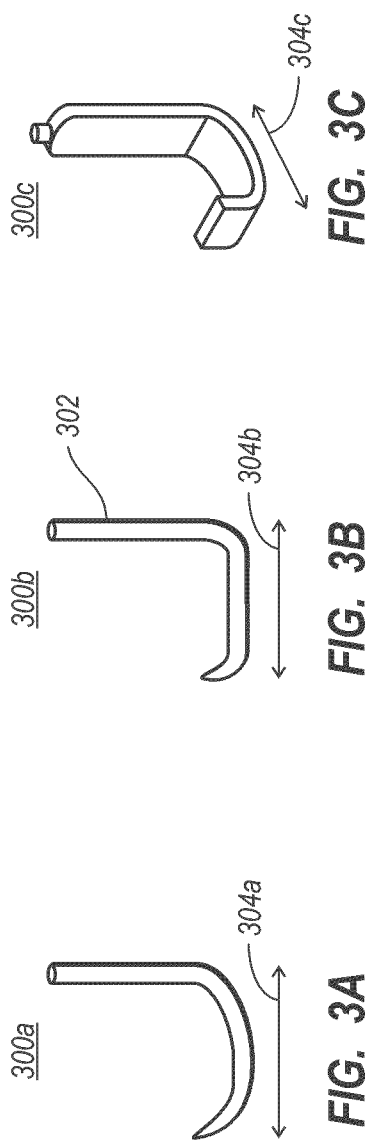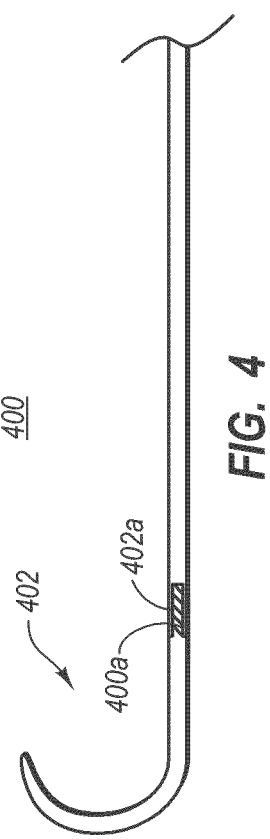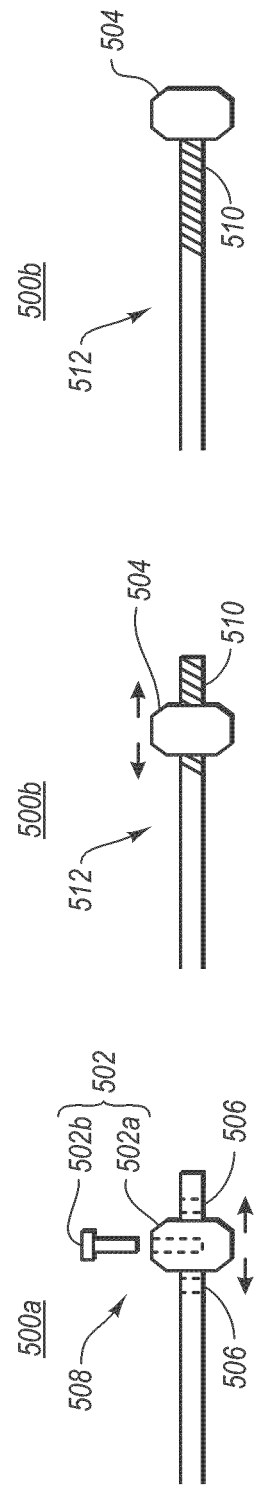

FIG. 6A
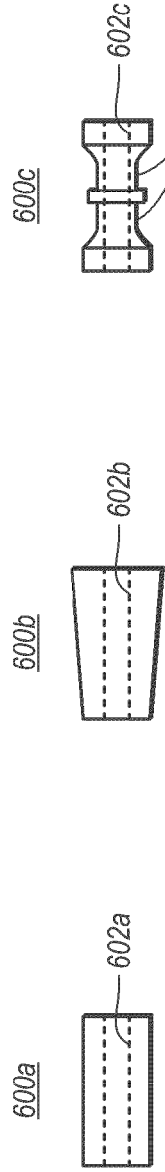
FIG. 6B
FIG. 6C
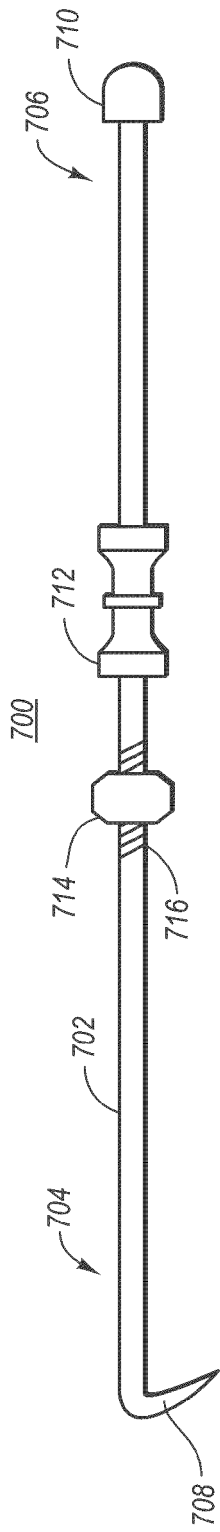
FIG. 7
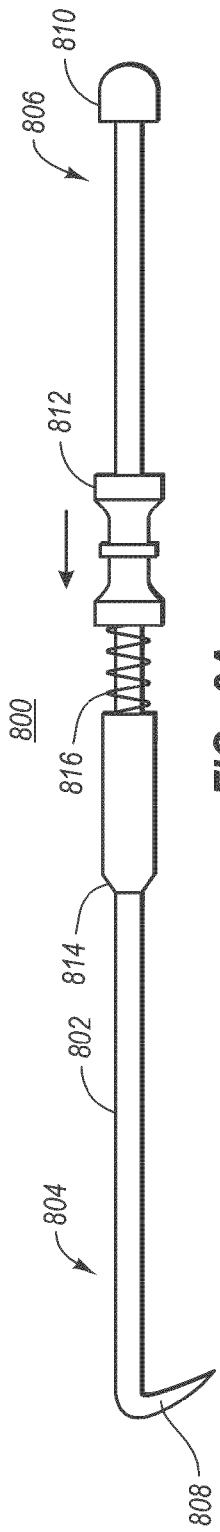
FIG. 8A
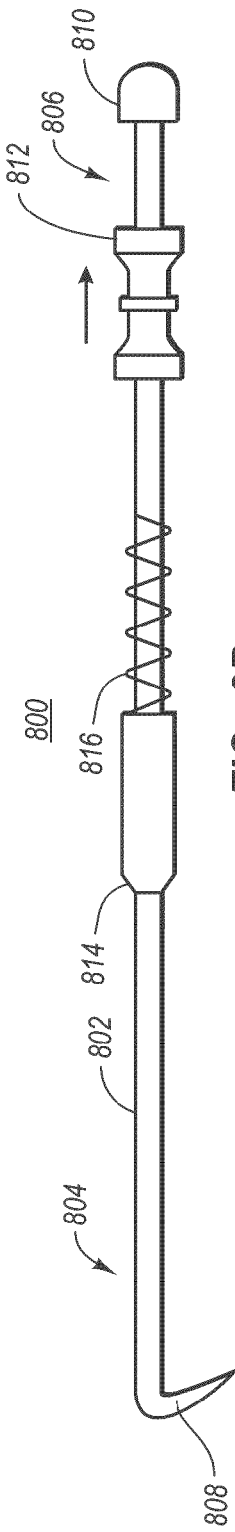
FIG. 8B

MEDICAL INSTRUMENTS FOR DIAPLASIS

TECHNICAL FIELD

The present disclosure relates to the field of medical devices.

BACKGROUND

Currently, in the diaplasis of fracture, e.g., zygomatic fracture, a single hook is generally used. However, it is sometimes difficult to obtain good diaplasis results just by depending on the single hook to retract the fractured bone segment, because human hands lack sufficient explosive force, or the force cannot be easily controlled once started. As a result, full traction reduction may not be achieved or the fractured ends may be over displaced under excessive force.

SUMMARY

In general, example embodiments relate to medical instruments. One example embodiment includes a medical instrument having a shaft and a movable element. The shaft has a first end and a second end. The first end includes an engaging member. The second end includes a stopping member. The movable element is configured to move along the shaft.

Another example embodiment includes a method of using a medical instrument. The method includes engaging a fractured bone segment with an engaging member included in a first end of a shaft of the medical instrument. The method also includes moving a movable element along the shaft towards a stopping member included in a second end of the shaft to create a force on the stopping member when the movable element comes in contact with the stopping member.

Yet another example embodiment includes a medical instrument having a shaft and a movable element. The shaft has a removably attachable first section and a removably attachable second section that are configured to be removably attached to each other. The removably attachable first section includes an engaging member. The removably attachable second section includes a first stopping member. The movable element has a through hole formed in it. The through hole has a shape that is complementary to a cross-sectional shape of at least a portion of the removably attachable second section. The movable element is configured to move along the at least a portion of the removably attachable second section.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 1A is an illustrative embodiment of a medical instrument.

FIG. 1B is a cross-sectional view of a portion of the medical instrument of FIG. 1A.

FIG. 1C is another embodiment of the cross-sectional view of FIG. 1B.

FIGS. 2A to 2H show illustrative embodiments of shafts that can be implemented in the medical instrument of FIG. 1A.

FIGS. 3A to 3C show illustrative embodiments of some engaging members that can be implemented in the medical instrument of FIG. 1A.

FIG. 4 is an illustrative embodiment of a shaft having a removably attachable first end that can be employed in the medical instrument of FIG. 1A.

FIGS. 5A to 5C show illustrative embodiments of shafts and removably attachable first stopping members that can be implemented in the medical instrument of FIG. 1A.

FIGS. 6A to 6C show some example movable elements that can be employed in the medical instrument of FIG. 1A.

FIG. 7 is a second illustrative embodiment of a medical instrument.

FIGS. 8A and 8B show a third illustrative embodiment of a medical instrument.

DETAILED DESCRIPTION

Figure 2F:
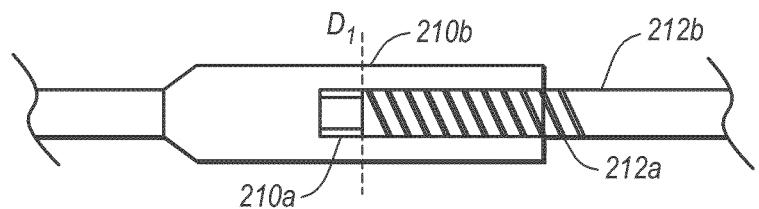

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Some embodiments include a medical instrument having a shaft and a movable element configured to move along the shaft. The shaft has a first end including an engaging member and a second end including a stopping member. As used herein, the term "engaging member" is to be construed broadly and may refer to a structure configured to provide contact with another structure, such as, but not limited to, a bone segment. Illustrative examples of such structures may include, but are not limited to, hooks, loops, picks, prongs, and shovel ends, among others.

In some embodiments, the engaging member is configured to engage a fractured bone segment of a subject. As used herein, the term "subject" should be broadly construed to include human subjects as well as animal subjects of all kinds such as, but not limited to, domesticated animals, zoo animals, farm animals, wild animals, endangered animals, race animals, working animals, pets, and aquatic animals. Illustrative examples of animals may include, but are not limited to, canines (e.g., dogs), felines (e.g., cats), equines (e.g., horses), birds, amphibians, reptiles, and other animal subjects. The movable element is moved along the shaft towards the stopping member. Upon coming in contact with the stopping member, the movable element applies a force to the stopping member, and hence to the engaging member via the shaft, for reduction of the fractured bone. Embodiments of the medical instrument can be applied to reduction of zygomatic fracture, e.g. zygomatic arch fracture, or other bone fractures.

I. First Example Medical Instrument

With reference first to FIG. 1A, one example of a medical instrument 100 according to some embodiments is disclosed. As shown, the medical instrument 100 includes a shaft 102 having a first end 104 and a second end 106. The first end 104 includes an engaging member 108. The second end 106 includes a first stopping member 110. The medical instrument additionally includes a movable element 112. Briefly, the movable element 112 is configured to move along at least a portion of the shaft 102 so as to contact the first stopping member 110 and impart a force to the first stopping member 110.

In some embodiments, the shaft 102 of the medical instrument 100 is a single piece lengthwise. For instance, the shaft 102 may be a single rod or pole made of steel, fiberglass, other suitable material(s), or any combination thereof. Alternatively, the shaft 102 may be made up of multiple strands or fibers that are arranged in parallel, braided, and/or twisted together.

In some embodiments, the shaft 102 has a substantially uniform diameter along its length. As such, the movable element 112 may be configured to move along substantially the entire length of the shaft 102 in some examples. In some other embodiments, the shaft 102 has a substantially uniform first diameter along a first section of the shaft 102 and a substantially uniform second diameter that is different than the first diameter along at least a second section of the shaft 102. As such, the movable element 112 may be configured to move along one or the other of the first and second sections of the shaft 102, but not along both of the first and second sections of the shaft 102.

In these and other examples, the shaft 102 may be originally formed as a single piece, or it may be made into a single piece by irremovably joining different parts thereof into an integral piece.

Alternatively, the shaft 102 may be composed of more than one section, as explained further below with respect to, e.g., FIGS. 2C-2E. For instance, in some embodiments, the shaft includes a first detachable section and a second detachable section that can be attached to each other. In some examples, the first and second detachable sections can be removably attached to each other, meaning the first and second detachable sections can be detached from each other and reattached to each other multiple times, if desired.

In this and other examples, the second detachable section may be screwed or clasped to the first detachable section. Alternatively or additionally, the second detachable section may be attached in other ways to the first detachable section using, for example, one or more pins, through holes, clips, nuts, bolts, adhesives, fasteners, or other mechanisms alone or in combination. In some embodiments, the medical instrument further comprises means for removably attaching the first detachable section and the second detachable section together.

In some embodiments, the attaching position of the second detachable section with respect to the first detachable section is adjustable in the length direction of the shaft 102, as explained in greater detail below with respect to, e.g., FIGS. 2C-2E. Briefly, for example, the second detachable section can be screwed onto the end of the first detachable section at any one of two or more positions determined at least by the pitch of the corresponding threads on the first and second detachable sections and the number of times the second detachable section is turned while being screwed onto the end of the first detachable section. As a result, some embodiments of the shaft are adjustable in length as described more fully below with respect to FIGS. 2C-2E.

In some embodiments, the shaft 102 has a substantially circular cross-sectional shape and the movable element 112 includes a cavity 114 having a complementary cross-sectional shape, as illustrated in FIG. 1B. FIG. 1B depicts a cross-section of the shaft 102 and movable element 112 of FIG. 1A along the cutting plane line 1B of FIG. 1A. As seen in FIG. 1B, the cross-sectional shape of the shaft 102 is substantially circular and the cross-sectional shape of the cavity 114 of the movable element 112 is also substantially circular and complementary to the cross-sectional shape of the shaft 102, allowing the movable element 112 to move lengthwise along at least a portion of the shaft 102.

In other embodiments, the shaft 102 has a non-circular cross-sectional shape, and the movable element 112 includes a cavity having a complementary non-circular cross-sectional shape to allow the movable element 112 to move along at least a portion of the shaft 102, while substantially preventing rotation of the movable element with respect to the shaft 102. For instance, FIG. 1C depicts a cross-section through an alternative shaft 102a and movable element 112a. As shown, the cross-sectional shape of the shaft 102a is substantially square and the cross-sectional shape of the cavity 114a of the movable element 112a is also substantially square and complementary to the cross-sectional shape of the shaft 102a, allowing the movable element 112a to move lengthwise along at least a portion of the shaft 102a.

Further, the non-circular shape of the cross-section of the shaft 102a substantially prevents the movable element 112a from rotating with respect to the shaft 102a. More particularly, the non-circular cross-sectional shape of the shaft 102 substantially prevents the movable element 112a from rotating about a center axis 116 of the shaft 102a independent of the shaft 102a.

It is understood that the substantially square cross-sectional shapes of the shaft 102a and the cavity 114a are only one example of non-circular cross-sectional shapes that can be employed to substantially prevent a movable element from rotating with respect to a shaft. Other examples of non-circular cross-sectional shapes include polygonal cross-sectional shapes such as rectangles, hexagons, or trapezoids, to name a few, and cross-sectional shapes that include combinations of curved and straight lines.

In the description that follows, each of the components of the medical instrument 100 and/or of additional components that can be implemented in some embodiments of a medical instrument will be described in greater detail below. For instance, various example ranges will be provided for one or more parameters of the components of the medical instrument 100, the parameters including one or more of length, width, diameter, mass, or the like. In some embodiments, the various components of the medical instrument 100 may be proportionately sized for the location, the bone, and/or the subject. It will be appreciated that the specific ranges discussed below are given by way of example only. Further, the values of the parameters may be varied to suit a particular application depending on, for example, the size of the subject and/or the bone to be fixed on the subject.

By way of example, a medical instrument 100 configured to reduce a fracture of a relatively large bone fragment and/or of a relatively large subject could have a shaft 102 having a length of about 40 centimeters (cm) and a diameter of about 1 cm, an engaging member 108 having a width of about 5 cm, and a movable element 112 having a mass of about 1000 grams (g). Alternatively, a medical instrument 100 configured to reduce a fracture of a relatively small bone fragment and/or of a relatively small subject could have a shaft 102 having a length of about 20 cm and a diameter of about 0.5 cm, an engaging member 108 having a width of about 3 cm, and a movable element 112 having a mass of about 20 grams (g). These are only two of numerous possible combinations.

A. Shafts

Turning next to FIGS. 2A-2E, some example shafts 200a, 200b, 200c, and 200d are illustrated that may correspond to the shaft 102 of FIG. 1A and that can be employed in a medical instrument, such as the medical instrument 100 of FIG. 1A. A length of the shafts 200a-200d may be in the range of about 20 centimeters (cm) to about 40 cm. In some examples, the length of the shafts 200a-200d is substantially equal to about 30 cm. In other examples the length of the shafts 200a-200d may be less than 20 cm or greater than 40 cm. A diameter of the shafts 200a-200d may be in the range of about 0.5 cm to about 1 cm. In other examples, the diameter of the shafts 200a-200d may be less than 0.5 cm or greater than 1 cm.

Although not required, the shafts 200a-200d may be formed from stainless steel, titanium alloy, fiberglass, wood, plastic, other suitable material(s), or any combination thereof. Further, the shafts 200a-200d may be disposable or reusable. Alternatively or additionally, the shafts 200a-200d may be sterilizable.

As shown in FIGS. 2A-2E, each of the shafts 200a, 200b, 200c, 200d, has, respectively, a first end 202a, 202b, 202c, 202d including an engaging member 204a, 204b, 204c, 204d.

In the examples illustrated in FIGS. 2A and 2B, the shafts 200a and 200b are each formed of a single section. The shaft 200a shown in FIG. 2A has a substantially uniform diameter over the length of the shaft 200a. As used herein, a shaft 200a is substantially uniform in diameter if the diameter of the shaft 200a remains constant along the length of the shaft 200a.

In comparison, the shaft 200b of FIG. 2B includes multiple portions with different diameters. In particular, the shaft 200b of FIG. 2B includes a first portion 206 with a first diameter and a second portion 208 with a second diameter different than the first diameter. For instance, the first portion 206 may have a diameter substantially equal to about 0.5 cm, while the second portion 208 may have a diameter substantially equal to about 1 cm.

FIG. 2C illustrates a shaft 200c comprising a first detachable section 210 and a second detachable section 212 that are configured to be removably attached to each other. As illustrated, the first detachable section 210 includes the first end 202c and engaging member 204c. Although not shown, the second detachable section 212 includes a corresponding second end and first stopping member.

As shown in FIG. 2C, the first detachable section 210 includes internal thread 210a at an end 210b opposite to the first end 202c of the shaft 200c, and the second detachable section 212 includes external thread 212a at a corresponding end 212b of the second detachable section 212 that can be removably engaged with the internal thread 210a of the first detachable section 210. Alternatively, the internal thread 210a may be formed in the end 212b of the second detachable section 212, and the external thread 212a may be formed on the end 210b of the first detachable section 131. In either configuration, the threaded end 210b of the first detachable section 210 and the threaded end 212b of the second detachable section 212 represent one example of a structural implementation of a means for removably attaching the first detachable section 210 and the second detachable section 212 together.

Figure 2G:
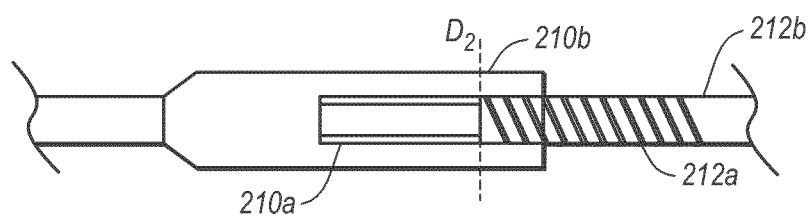

In some embodiments, the length of the shaft 200c can be adjusted by varying the depth by which the external thread 212a is engaged with the internal thread 210a. For instance, FIG. 2F illustrates an example where the external thread 212a is engaged with the internal thread 210a to a depth $D_1$, while FIG. 2G illustrates an example where the external thread 212a is engaged with the internal thread 210a to a depth $D_2$. Depending on whether the external thread 212a is engaged with the internal thread 210a to the depth $D_1$ or $D_2$, or any other depth, the length of the shaft 200c will be adjusted accordingly.

Although not required in all embodiments, as shown in FIG. 2C, the end 210b of the first detachable section 210 has a larger diameter than the other portion of shaft 200c. Alternatively or additionally, the end 212b of the second detachable section 212 can have a larger diameter than the other portion of the shaft 200c. In either configuration, the portion having the larger diameter may serve as a handle portion which facilitates grasping of the shaft 200c. Alternatively or additionally, the portion having the larger diameter may serve as a second stopping member to confine a corresponding movable element to motion along the second detachable section 212. Second stopping members are described in greater detail below with respect to FIGS. 7-10B.

In some embodiments, the portion having the larger diameter can include a pattern or coating on its surface to prevent slippage during grasping of the shaft 200c. For instance, a plurality of depressions, e.g., dimples, can be formed in a pattern on the surface of the portion having the larger diameter. Alternatively or additionally, a plurality of protrusions can be formed in a pattern on the surface of the portion having the larger diameter. Alternatively or additionally, a rubber or latex coating can be applied to the surface of the portion having the larger diameter.

Similar to FIG. 2C, FIGS. 2D and 2E illustrate a shaft 200d that includes two detachable sections 214, 216. In particular, FIG. 2D illustrates the shaft 200d in an assembled configuration, while FIG. 2E illustrates the shaft 200d in a disassembled configuration. As illustrated, the first detachable section 214 includes the first end 202d and engaging member 204d. Although not shown, the second detachable section 216 includes a corresponding second end and first stopping member.

In the example of FIGS. 2D and 2E, a plurality of retaining slots 214a are provided at an end 214b of the first detachable section 214 opposite to the first end 202d of the shaft 200d. In some embodiments, each retaining slot 214a is a recessed cavity. Alternatively, each of the retaining slots 214a may comprise a through hole formed in the end 214b of the first detachable section 214, or a tapped hole formed in the end 214b of the first detachable section 214.

Each retaining slot 214a is configured to receive a flange, pin, or fastener 216a provided at an end 216b of the second detachable section 216 and to retain the flange 216a so as to clasp the second detachable section 216 to the first detachable section 214. Alternatively, the retaining slots 214a may be formed in the end 216b of the second detachable section 216 and the flange 216a may be provided at the end 214b of the first detachable section 214. In either configuration, the retaining slot(s) 214a and the flange 216a represent an example of a structural implementation of a means for removably attaching the first detachable section 214 and the second detachable section 216 together.

In some embodiments, the length of the shaft 200d can be adjusted by inserting the flange 216a into a different one of the retaining slots 214a. Alternatively, the first detachable section 214 can include a single retaining slot 214a such that the length of the shaft 200d is not adjustable while still permitting the first and second detachable sections 214, 216 to be removably attached to each other.

Figure 2H:
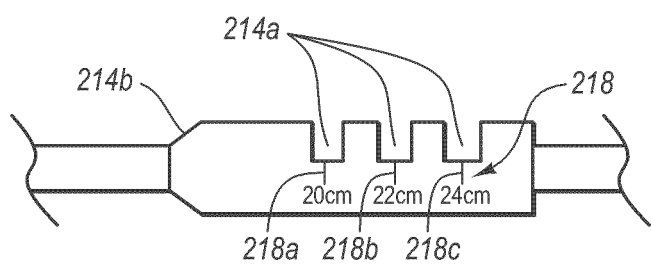

Although not required in all embodiments, in some embodiments the shafts 200c and 200d can include scale marks on at least part of the shaft 200c, 200d to provide a reference for adjusting the length of the shaft 200c, 200d. For example, FIG. 2H illustrates an example of the end 214b of the first detachable section 214 of the shaft 200d of FIGS. 2D-2E. As shown in FIG. 2H, a scale 218 is provided on the end 214b indicating a length of the shaft 200d when the flange 216a is received by a corresponding retaining slot 214a. In the illustrated embodiment of FIG. 2H, the length of the shaft 200d is about 20 cm when the flange 216a is received in the left-most slot 214a, as indicated by scale mark 218a, the length of the shaft 200d is about 22 cm when the flange 216a is received in the middle slot 214a, as indicated by scale mark 218b, and the length of the shaft 200d is about 24 cm when the flange 216a is received in the right-most slot 214a, as indicated by scale mark 218c. In other embodiments, the scale 218 may be provided in other forms and/or with different incrementation and labeling.

Adjustable shaft 200c, 200d lengths can provide a corresponding movable element, such as the movable element 112 of FIG. 1A, with different moving lengths along the shaft 200c, 200d.

B. Engaging Members and First Ends

With additional reference to FIGS. 3A, 3B and 3C, some example engaging members 300a, 300b, 300c are illustrated that may correspond to the engaging member 108 of FIG. 1A and that can be implemented in the first end of a medical instrument, such as in the first end 104 of the medical instrument 100 of FIG. 1A. The engaging members 300a, 300b, 300c have a variety of configurations. For instance, as shown in FIG. 3A, the engaging member 300a is curved, whereas the engaging member 300b of FIG. 3B substantially forms an angle of about 90° with respect to a corresponding shaft 302, and the engaging member 300c of FIG. 3C takes a form of a flat hook which has a thin elongated cross-section. The configurations of FIGS. 3A-3C can be combined and/or rearranged.

Alternatively, an engaging member may include a stick-like structure that has been screwed, pinned, welded, or otherwise attached to or formed on a first end of a shaft in a tau or "T" shaped configuration.

In some embodiments, a width 304a, 304b, 304c of the engaging members 300a, 300b, 300c is in the range of about 3 cm to about 5 cm. In some other embodiments, the widths 304a, 304b, 304c of engaging members 300a, 300b, 300c is less than 3 cm or more than 5 cm.

Returning to FIG. 1A, and as mentioned above, the first end 104 of the shaft 102 may be formed integrally with or irremovably fixed to the shaft 102. Alternatively, the first end 104 of the shaft 102 may be removably attached to the shaft 102, and thus can be removed for, e.g., sterilization, and/or replaced as needed.

For instance, FIG. 4 illustrates an embodiment of a shaft 400 including a removable first end 402. As shown in FIG. 4, the first end 402 is formed with external thread 402a which may be engaged with corresponding internal thread 400a formed in the shaft 400. In some other embodiments, both of the first end 402 and the shaft 400 may be provided with external thread so that they can be removably attached together by using a screw nut configured to engage both of them. In this and other embodiments, the ability to removably attach the first end 402 to the shaft 400 allows the shaft 400 to be used with any one of multiple first ends 402 of different forms, sizes and/or materials to offer a user the opportunity of replacing the first end to suit different applications and/or as otherwise desired. For instance, one first end 402 may include a curved engaging member such as depicted in FIG. 3A, another first end 402 may include a 90° angle engaging member such as illustrated in FIG. 3B, and yet another first end 402 may include a flat hook engaging member such as shown in FIG. 3C. Each of the different first ends 402 may be suited for one or more different uses. A collection of multiple and/or varying first ends 402 together with other parts of a corresponding medical instrument may form a kit.

It will be appreciated, with the benefit of the present disclosure, that the different embodiments disclosed herein can be combined together and/or implemented separately. For instance, removable first ends 402 can be implemented in conjunction with one piece shafts, such as the shafts 200a, 200b of FIGS. 2A and 2B, or in conjunction with shafts having multiple detachable sections, such as the shafts 200c and 200d of FIGS. 2C-2E.

C. First Stopping Members

Returning to FIG. 1A, the first stopping member 110 may be formed integrally with the shaft 102, the first stopping member 110 may be fixedly secured to the shaft 102, or the first stopping member 110 may be removably attached to the shaft 102. In some embodiments, the first stopping member 110 is glued, welded, screwed or pinned to the shaft 102. In some embodiments, the medical instrument 100 further comprises means for removably attaching the first stopping member 110 to the shaft 102. Alternatively or additionally, the attaching position of the first stopping member 110 with respect to the shaft 102 may be adjustable along the length of the shaft 102.

For example, FIGS. 5A and 5B illustrate example shafts 500a, 500b and first stopping members 502, 504 that may respectively correspond to the shaft 102 and first stopping member 110 of FIG. 1A. For the sake of clarity, only part of the shaft 500a, 500b and the first stopping member 502, 504 are shown in FIGS. 5A and 5B. In the examples of FIGS. 5A and 5B, each first stopping member 502, 504 is removably attachable to shaft 500a, 500b, respectively.

In the example of FIG. 5A, the first stopping member 502 includes a main body 502a and a pin 502b configured to be inserted through a hole in the main body 502a. The main body 502a may have a variety of shapes, including a circular cylinder shape, a hexagonal shape, a cube or other rectangular box shape, or the like or any combination thereof.

At least one pin hole 506 is formed in a second end 508 of the shaft 500a, to which the first stopping member 502 is attached. The at least one pin hole 506 is arranged along the length direction of the shaft 500a. In some embodiments in which a plurality of pin holes 506 are formed in the second end 508, the attaching position of the first stopping member 502 with respect to the shaft 500a can be adjusted by inserting the pin 502b into a different one of the pin holes 506 along the length of the shaft 410. The pin 502b, the hole in the main body 502a, and the pin hole 506 represent one example of a structural implementation of a means for removably attaching the first stopping member 502 to the shaft 500a.

In some embodiments, internal threads are provided within the pin hole 506. As such, a threaded bolt or screw, rather than the pin 502b, can be provided for removably attaching the main body 502a to the shaft 500a.

In the example of FIG. 5B, the first stopping member 504 is in a form of a nut having internal thread, which can be engaged with external thread 510 formed on a second end 512 of the shaft 500b. As such, the first stopping member 504 may have a hexagonal shape, or other shapes such as a circular cylinder, cube, or rectangular box shape. Alternatively or additionally, the first stopping member 504 can be in a form of a cap nut.

In some embodiments, the attaching position of the first stopping member 504 with respect to the shaft 500b can be adjusted by screwing the first stopping member 504 in or out with respect to the shaft 500b. More particularly, and analogous to the explanation give above with respect to FIGS. 2F and 2G, the position of the first stopping member 504 can be adjusted by the internal thread of the first stopping member 504 engaging the external thread 510 to different depths. The internal thread of the first stopping member 504 and the external thread of the shaft 500b represent one example of a structural implementation of a means for removably attaching the first stopping member 504 to the shaft 500b.

FIGS. 5A and 5B illustrate examples of first stopping members 502, 504 that can be removably attached to shafts 500a, 500b using a pin 502b and pin hole 506 in the example of FIG. 5A, and using internal and external threads in the example of FIG. 5B. Alternatively or additionally, first stopping members are removably attached to shafts using one or more pins, pin holes, internal thread, external thread, screws, bolts, nuts, retaining clips, or other mechanisms implemented individually or in any combination.

As illustrated in FIGS. 5A and 5B, some embodiments allow the position of first stopping members 502, 504 to be adjusted with respect to shafts 500a, 500b. Adjustable first stopping members 502, 504 can provide a corresponding movable element, such as the movable element 112 of FIG. 1A, with different moving lengths along the shaft 500a, 500b.

For example, FIG. 5C illustrates the shaft 500b with the first stopping member 504 positioned substantially at the end of second end 512. In comparison with the configuration of FIG. 5B, the configuration of FIG. 5C increases the length along the shaft 500b over which a corresponding movable element can travel.

The force generated by a corresponding movable element on the first stopping members 502, 504 may at least partially depend on the length of the shaft 500a, 500b over which the corresponding movable element is allowed to move. As such, the use of adjustable first stopping members 502, 504 may permit adjustment of the force generated by the corresponding movable element on the first stopping member 502, 504 during operation.

The first stopping member 502, 504 may be of any shape and size configured to stop the movement of the corresponding movable element stably to generate a force. In some embodiments, the first stopping member 502, 504 has a flat surface facing a corresponding first end of the shaft 500a, 500b with at least one dimension along the flat surface that is greater than that of the movable element so as to substantially stop forward movement of the movable element when it contacts the first stopping member 502, 504. The first stopping member may be made of metal, plastic, and/or other suitable material(s).

D. Movable Elements

Turning next to FIGS. 6A, 6B, and 6C, some example movable elements 600a, 600b, 600c are illustrated that may correspond to the movable element 112 of FIG. 1A and that can be implemented in a corresponding medical instrument, such as the medical instrument 100 of FIG. 1A.

The movable element 600a shown in FIG. 6A generally has a cylindrical shape with a through-hole 602a formed in the axial direction of the movable element 600a. As such, the movable element 600a may have a cross-sectional outer perimeter that is substantially circular in shape, such as shown in FIGS. 1A and 1B with respect to movable elements 112, 112a.

The movable element 600b shown in FIG. 6B generally has a frustoconical shape (e.g., a truncated cone) with a through-hole 602b formed in the axial direction of the movable element 600b. As such, the movable element 600b may also have a cross-sectional outer perimeter that is also substantially circular in shape, although the diameter of the movable element 600b may vary linearly along the length of the movable element 600b.

The movable element 600c shown in FIG. 6C has a through-hole 602c formed in the axial direction of the movable element 600c and further includes contours 604 formed on its outer surface.

FIGS. 6A, 6B and 6C illustrate movable elements 600a, 600b, 600c having particular shapes, including cylindrical, frustoconical, and contoured. In each of these examples, the movable elements 600a-600c may have cross-sectional outer perimeters that are substantially circular in shape, such as illustrated in FIGS. 1A and 1B. However, the shapes of the cross-sectional outer perimeters of movable elements 600a, 600b, 600c illustrated in FIGS. 6A, 6B and 6C should not be construed to be limiting. For example, movable elements according to some embodiments can have cross-sectional outer perimeters of other shapes such as polygonal, including rectangular, triangular, hexagonal, trapezoidal, etc., or a combination of curved and straight lines. Further, the movable elements 600a, 600b, 600c may have different sizes according to a particular usage.

More generally, the movable element 600a, 600b, 600c may be a mass of any shape having a through hole formed therein, where the through hole has a cross-sectional shape that is complementary to the cross-sectional shape of the corresponding shaft along which the movable element 600a, 600b, 600c moves, as illustrated and described above with respect to FIGS. 1A and 1B. Alternatively or additionally, surface textures, contours, dents or coatings may be provided on the outer surface of the movable element 600a, 600b, 600c to facilitate the manipulation of the movable element 600a, 600b, 600c. For instance, the outer surface of the movable element 600a, 600b, 600c can include a plurality of depressions or a plurality of protrusions formed thereon, a rubber or latex coating applied thereon, or the like or any combination thereof.

Further, the mass of the movable element 600a, 600b, 600c may be configured to suit a particular application. In some embodiments, the mass of the movable element 600a, 600b, 600c is in the range of about 20 g to about 1000 g. Specifically, the mass of the movable element 600a, 600b, 600c may be in the range of about 100 g to about 500 g. In some embodiments, the mass of the movable element 600a, 600b, 600c is about 200 g. In other embodiments, the mass of the movable element 600a, 600b, 600c is less than 20 g or more than 1000 g. In embodiments that include shafts with removable first stopping members, such as the shafts 500a, 500b of FIGS. 5A and 5B, the movable element 600a, 600b, 600c can be assembled with and dissembled from the corresponding shaft 500a, 500b at the second end 508, 512 of the shaft 500a, 500b. For instance, with the first stopping member 502, 504 removed from shafts 500a, 500b, movable element 600a, 600b, or 600c could be assembled onto shaft 500a, 500b and then the movable element 600a, 600b, or 600c could be attached to the shaft 500a, 500b to prevent the movable element 600a, 600b, or 600c from being removed. To remove the movable element 600a, 600b, or 600c from shaft 500a, 500b, the first stopping member 502, 504 could then be removed from the shaft 500a, 500b.

Alternatively or additionally, in embodiments that include shafts with first and second detachable sections, such as shafts 200c, 200d of FIGS. 2C-2E, the movable element 600a, 600b, 600c can be assembled with and dissembled from the corresponding shaft 200c, 200d by first disengaging the first detachable section 210, 214 from the second detachable section 212, 216 of the shaft 200c, 200d. For example, with the first detachable section 210, 214 disengaged from the second detachable section 212, 216, the movable element 600a, 600b, 600c could be assembled onto the second detachable section 212, 216, and then the first detachable section 210, 214 and second detachable section 212, 216 could be attached together to prevent the movable element 600a, 600b, or 600c from being removed. To remove the movable element 600a, 600b, 600c, the first detachable section 210, 214 and second detachable section 212, 216 would be detached from each other.

Accordingly, a collection of movable elements 600a, 600b, 600c of different shapes, surface features and/or masses together with other parts of a corresponding medical instrument may form a kit.

Further, each of the different components of the medical instrument described herein may be formed from one or more of stainless steel, titanium alloy, plastic, medical ceramic, or other suitable material(s).

II. Example Method of Medical Instrument Use

Medical instruments according to some embodiments can be used in a variety of ways. In one example method, and with reference to FIG. 1A, a fractured bone segment (not shown) is engaged by the engaging member 108. Engaging the fractured bone segment with the engaging member 108 may include making the engaging member 108 hook on the fractured bone segment. The movable element 112 is moved along the shaft 102 towards the first stopping member 110 to create a force on the first stopping member 110 when the movable element 112 contacts the first stopping member 110. Upon coming in contact with the stopping member, the movable element applies a force to the stopping member, and hence to the engaging member via the shaft, for reduction of the fractured bone. In some embodiments, the force may be at least partially controlled by one or more of the following factors: the mass of the movable element 112, the moving length of the movable element 112 along the shaft 102, the moving speed of the movable element 112 towards the first stopping member 110, the force to move the movable element 112 towards the first stopping member 110 exerted by a user of the medical instrument 100 or generated by a spring provided on the shaft as will be explained below with reference to FIGS. 8A-8B and 10A-10B. Those skilled in the art will understand, however, that manual manipulation of the movable element and spring-based operation are only illustrative examples of implementation of moving the movable element. Alternatively or additionally, automatic control means, such as, but not limited to, digital setting, pre-programmed protocol, real-time control and intelligent adjustment may be involved to different extents. Other embodiments will be apparent to those skilled in the art.

Alternatively or additionally, and with additional reference to FIG. 4, the method may include attaching the first end 402 to the shaft 400. In some embodiments, attaching the first end 402 to the shaft 400 may include screwing an external thread 402a formed in one of the first end 402 and the shaft 400 into an internal thread 400a formed on the other one of the shaft 400 or first end 402, or it may include engaging a nut with external threads formed on both of the first end 402 and the shaft 400 to attach them to each other.

Alternatively or additionally, and with additional reference to FIGS. 2C-2E, the method may include attaching the second detachable section 212, 216 and the first detachable section 210, 214 together. The method may include adjusting the attaching position of the second detachable section 212, 216 with respect to the first detachable section 210, 214. In some embodiments, attaching the second detachable section 212 and the first detachable section 210 together may include attaching them by thread engagement, and the attaching position is adjustable by changing the depth by which the thread engagement advances. In other embodiments, the attaching of the second detachable section 216 and the first detachable section 214 together may include inserting a flange 216a formed on an end of one the two sections 216, 214 into a retaining slot 214a formed in an end of the other one of the two sections 214, 216. In this case, the attaching position may be adjusted by relocating the flange 216a to another retaining slot 214a.

Alternatively or additionally, and with additional reference to FIGS. 5A and 5B, the method may include attaching the first stopping member 502, 504 to the shaft 500a, 500b. The method may include adjusting the attaching position of the first stopping member 502, 504 with respect to the shaft 500a, 500b. In some embodiments, attaching the first stopping member 502 to the shaft 500a may include inserting a pin 502b through the first stopping member 502 into a corresponding hole 506 formed in the shaft 500a, and adjusting the attaching position may include relocating the pin 502b through the first stopping member 502 into a different hole 506. In other embodiments, attaching the first stopping member 504 to the shaft 500b may include screwing the first stopping member 504 onto the shaft 500b, and adjusting the attaching position may include screwing the first stopping member 504 further in or out.

Alternatively or additionally, as will be explained below with reference to FIGS. 9A and 9B, the method may include locking a movable element with respect to a corresponding shaft. The locking may include engaging a locking bolt which goes through the movable element into a locking hole in the shaft.

Alternatively or additionally, as will be explained below with reference to FIGS. 8A-8B and 10A-10B, moving a movable element along a corresponding shaft may include biasing or compressing a spring by pushing the movable element against the spring and then releasing the movable element.

Alternatively or additionally, the method may include selecting a movable element from among a set of movable elements.

III. Second Example Medical Instrument

FIG. 7 shows a second example embodiment of a medical instrument 700 having a shaft 702 with a first end 704 and a second end 706. The first end 704 includes an engaging member 708 and the second end 706 includes a first stopping member 710. The medical instrument 700 also includes a movable element 712 and a second stopping member 714. As shown in FIG. 7, the second stopping member 714 is positioned on the shaft 702. The second stopping member 714 is configured to cooperate with the first stopping member 710 to confine the movable element 712 between the first stopping member 710 and the second stopping member 714 along the shaft 702. In some embodiments, the second stopping member 714 is configured to be removably attached to the shaft 702 at any one of a plurality of positions. In the illustrated embodiment, the second stopping member 714 is screwed onto external thread 716 provided on the shaft 702. The attaching position of the second stopping member 714 with respect to the shaft 702 is adjustable in the length direction of the shaft 702 in this example by screwing the second stopping member 714 in or out. As a result, the range over which the movable element 712 is allowed to move along the shaft 702 can be adjusted. Alternatively, the second stopping member 714 can be formed as an integral part of the shaft 702 having a diameter that is larger than a diameter of the portion of the shaft 702 over which the movable element 712 is configured to move. Alternatively or additionally, the second stopping member 714 can be attached to the shaft 702 in a manner that does not permit adjustment of the attaching position of the second stopping member 714 with respect to the shaft 702. In some embodiments, the medical instrument 700 further comprises means for removably attaching the second stopping member 714 to the shaft 702.

In FIG. 7, the second stopping member 714 is shown as a separately provided element. In other embodiments, the second stopping member 714 is integral with one or more other components of the medical instrument 700. For example, in FIG. 2C, the end 210*b* of the first detachable section 210 of shaft 200*c* can function as a second stopping member. Alternatively, in FIGS. 2D and 2E, the end 214*b* of first detachable section 214 of shaft 200*d* can function as a second stopping member. Other configurations are also contemplated. As such, in the embodiment of FIG. 7, the forms of the shaft 702, the first end 704, the movable element 712, the first stopping member 710, and the second stopping member 714 are given by way of example, and not by way of limitation.

One or more of the embodiments described above with respect to FIGS. 2A-6C can be combined with the embodiment of FIG. 7.

IV. Third Example Medical Instrument

FIGS. 8A and 8B show a third example embodiment of a medical instrument 800 having a shaft 802 with a first end 804 and a second end 806. The first end 804 includes an engaging member 808 and the second end 806 includes a first stopping member 810. The medical instrument 800 also includes a movable element 812, a second stopping member 814, and a spring 816 provided between the second stopping member 814 and the movable element 812. In this and other examples, the spring 816 is provided to energize the movement of the movable element 812 along the shaft 802. FIG. 8A shows a state in which the movable element 812 is pushed against the spring 816 to bias the spring 816, and FIG. 8B shows a state in which the movable element 812 is energized by the spring 816 to move toward the first stopping member 810 after the movable element 812 is released.

One or more of the embodiments described above with respect to FIGS. 2A-7 can be combined with the embodiment of FIGS. 8A and 8B. In some embodiments, the spring 816 is a helical spring which is guided by the shaft 802 to contract and expand.

During reduction of fracture, such as reduction of zygomatic fracture, after engaging the bone fracture segment with the engaging member 808, the movable element 812 may be pushed against the spring 816 to bias the spring 816 against the second stopping member 814, thereby compressing the spring 816. Then, when the movable element 812 is released, the compressed spring 816 expands and energizes the movable element 812 to move toward the first stopping member 810 and generate a force thereon. The spring 816 may be selected from among multiple springs having different elastic coefficients, lengths or other properties, so as to provide force of different levels as suited or desired for different applications.

V. Fourth Example Medical Instrument

Figure 9A:
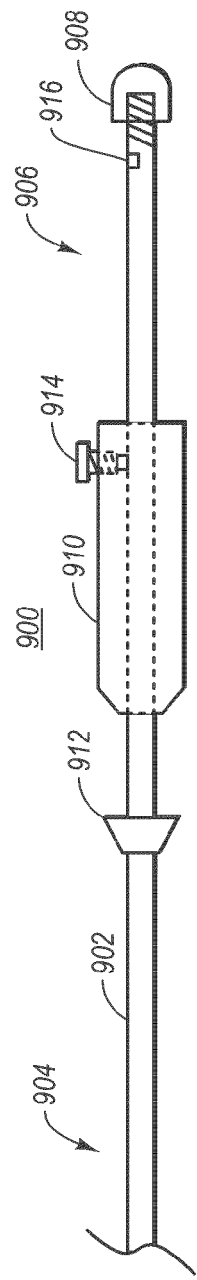
FIGS. 9A and 9B show a fourth illustrative embodiment of a medical instrument.
Figure 9B:
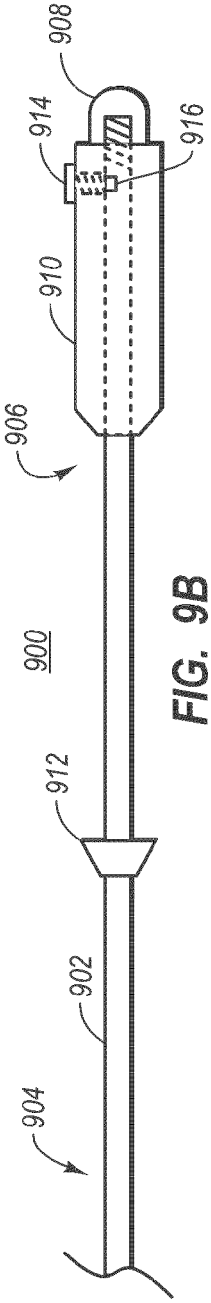

FIGS. 9A and 9B show a fourth example embodiment of a medical instrument 900 having a shaft 902 with a first end 904 and a second end 906. The second end 906 includes a first stopping member 908. The medical instrument 900 also includes a movable element 910, a second stopping member 912, and a locking mechanism configured to lock the movable element 910 to the shaft 902. FIG. 9A shows a state in which the movable element 910 is movable with respect to the shaft 902, and FIG. 9B shows a state in which the movable element 910 is locked with respect to the shaft 902.

The locking mechanism can lock the movable element 910 to the shaft 902 so as to prevent movement of the movable element 910 with respect to the shaft 902. In some embodiments, the movable element 910 may be locked to the shaft 902 during transportation so as to avoid movement of the movable element 910 that might damage the shaft 902 or other components of the medical instrument 900, or to ease transportation and avoid undesirable noises. In other embodiments, the movable element 910 may be locked to the shaft 902 during use so that movement of the movable element 910 with respect to the shaft 902 can be substantially prevented after reduction of a fractured bone segment is performed.

As shown in FIGS. 9A and 9B, the locking mechanism includes a locking bolt 914 that is screwed into a threaded hole of the movable element 910, and a locking hole 916 formed in the second end 906 of the shaft 902. As best seen in FIG. 9A, when the locking bolt 914 is not engaged with the locking hole 916 of the shaft 902, the movable element 910 can move along the shaft 902. When the movable element 910 is positioned to align the threaded hole of the movable element 910 with the locking hole 916 of the shaft 902, the locking bolt 914 can be screwed in to engage with the locking hole 916, so that the movable element 910 is locked in the length direction of the shaft 902.

In FIG. 9A, the locking bolt 914 remains in the threaded hole of the movable element 910 while the movable element 910 is free to move along the shaft 902. In some other embodiments, the locking bolt 914 is removed from the threaded hole of the movable element 910.

It will be appreciated, with the benefit of the present disclosure, that other locking mechanisms can be employed to lock the movable element 910 to the shaft 902. For example, one or more screws, bolts, nuts, through holes, pins, retaining clips, straps, fasteners, or other mechanisms, used alone or in any combination, can be employed to lock the movable element 910 to the shaft 902.

According to this and other embodiments, the movable element 910 can be used as a handle portion when it is locked with respect to the shaft 902. Thus, the locking mechanism may facilitate convenient switching between the usage of a human hand force and a force generated by the movable element 910 on the first stopping member 908 during use of the medical instrument 900.

In the embodiment of FIGS. 9A and 9B, the locking hole 916 is formed in the shaft 902 near the first stopping member 908. In other embodiments, the locking hole 916 can be formed in other areas of the shaft 902.

One or more of the embodiments described above with respect to FIGS. 2A-8B can be combined with the embodiment of FIGS. 9A and 9B.

In some embodiments, to substantially prevent the locking bolt 914 from being circumferentially offset about the shaft 902 from the locking hole 916, at least part of the shaft 902, along which the movable element 910 is configured to move, has a non-circular cross-sectional shape, such that the movable element 910 cannot rotate about the shaft 902. One example of a shaft 102a having a non-circular cross-sectional shape configured to prevent rotation of a movable element 112a about the shaft 102a is provided in FIG. 1C.

More generally, such non-circular cross-sectional shapes for the shaft 902 may include, but are not limited to, polygonal cross-sectional shapes such as rectangles, hexagons, or trapezoids, and cross-sectional shapes that include combinations of curved and straight lines. In some embodiments, a first portion of the shaft 902 between the first and the second stopping members 908 and 912 may have a non-circular cross-sectional shape, and a second portion of the shaft 902 that extends from the second stopping member 912 to the first end 904 of the shaft 902 may have a circular cross-sectional shape.

VI. Fifth Example Medical Instrument

Figure 10A:
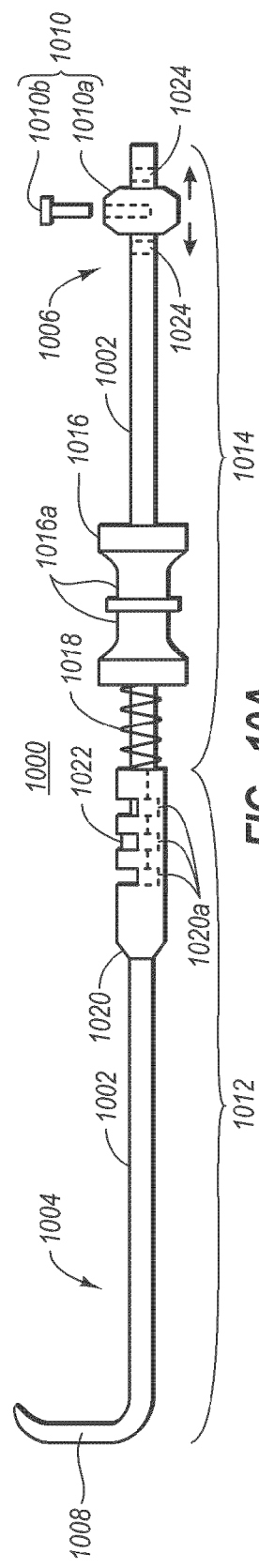
FIGS. 10A and 10B show a fifth illustrative embodiment of a medical instrument.
Figure 10B:
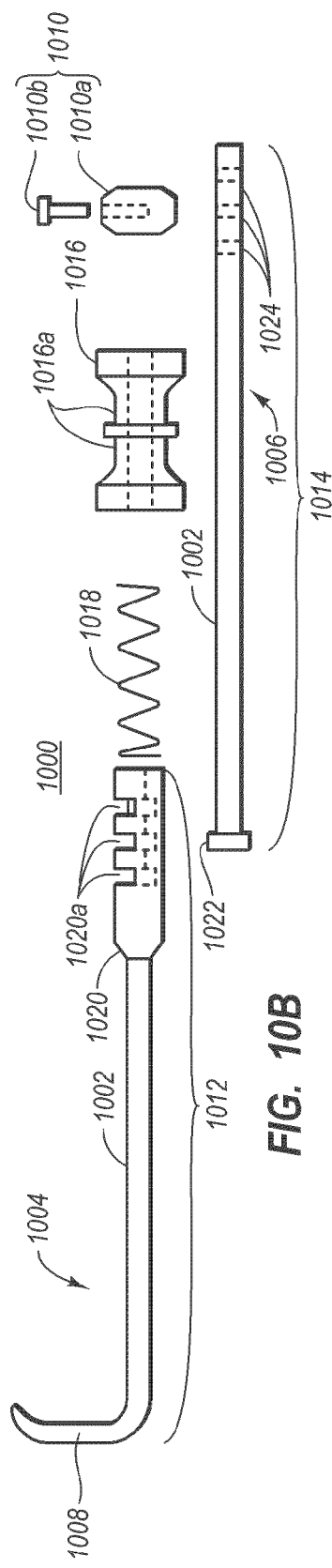

FIGS. 10A and 10B show a fifth example embodiment of a medical instrument 1000 having a shaft 1002 with a first end 1004 and a second end 1006. The first end includes an engaging member 1008 and the second end 1006 includes a first stopping member 1010. The shaft 1002 includes multiple sections, including a first detachable section 1012 and a second detachable section 1014. The medical instrument 1000 also includes a movable element 1016 and a spring 1018. FIG. 10A shows an assembled state of the medical instrument 1000, and FIG. 10B shows a disassembled state of the medical instrument 1000.

One or more of the embodiments described above with respect to FIGS. 2A-9B can be combined with the embodiment of FIGS. 10A and 10B. Indeed, the embodiment of FIGS. 10A and 10B includes a first detachable section 1012 and a second detachable section 1014 that are analogous to the first detachable section 214 and second detachable section 216 of FIGS. 2D and 2E, while also including a removably attachable first stopping member 1010 that is analogous to the removably attachable first stopping member 502 of FIG. 5A, and various other components disclosed with respect to some of the other Figures included herein. Components of the medical instrument 1000 of FIGS. 10A and 10B that are analogous to components already described above will not be described in detail below.

As shown, the first detachable section 1012 includes an end 1020 in which a plurality of retaining slots 1020a are formed and arranged in the length direction of the shaft 1002. Each retaining slot 1020a is a recessed cavity corresponding to the shape of a flange 1022 formed at one end of the second detachable section 1014, and can retain the flange 1022 so as to clasp the second detachable section 1014 and the first detachable section 1012 together. The attaching position of the second detachable section 1014 with respect to the first detachable section 1012 can be adjusted by relocating the flange 1022 into a different one of the retaining slots 1020a. Thus, the range over which the movable element 1016 is allowed to move along the shaft 1002 can be adjusted.

In this example, the first stopping member 1010 includes a main body 1010a and a pin 1010b. The second end 1006 of the shaft 1002, that is, the end of the second detachable section 1014 that is not to be engaged with the first detachable section 1012 in this example, is formed with a plurality of pin holes 1024. These pin holes 1024 are arranged in the length direction of the shaft 1002. Each pin hole 1024 can receive the pin 1010b of the first stopping member 1010, so as to attach the first stopping member 1010 to the second detachable section 1014 at the second end 1006 of the shaft 1002. The attaching position of the first stopping member 1010 with respect to the shaft 1002 can be adjusted by relocating the pin 1010b with a different one of the pin holes 1024.

Scale marks, such as the scale marks 218 of FIG. 2H, may be provided on the shaft 1002. For example, scale marks can be provided between the flange 1022 and pin holes 1024. Thus, the range over which the movable element 1016 is allowed to move along the shaft 1002 can be adjusted with the aid of the scale marks.

The movable element 1016 is generally cylindrical in shape, and has contours 1016a formed on the outer circumferential surface thereof for easier manipulating of the movable element 1016 by fingers.

The spring 1018 is positioned between the end 1020 of the first detachable section 1012 and the movable element 1016. The spring 1018 is a helical spring guided by the second detachable section 1014. During reduction of fracture, after engaging a fractured bone segment with the engaging member 1008, the movable element 1016 may be pushed against the spring 1018 to compress the spring 1018 against the end 1020 of the first detachable section 1012. Then, when the movable element 1016 is released, the compressed spring expands and energizes the movable element 1016 to move toward the first stopping member 1010 and generate a force thereon.

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g. bodies of the appended claims) are generally intended as "open" terms (e.g. the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g. "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g. the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g. "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g. "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A medical instrument, comprising:
   a shaft including:
      a first elongated section including an engaging member at a first end of the first elongated section and an aperture in a second end of the first elongated section that is opposite the first end of the first elongated section, the aperture including internal threading and the engaging member comprising a hook; and
      a second elongated section including a stopping member at a first end of the second elongated section and external threading at a second end of the second elongated section that is opposite the first end of the second elongated section, the stopping member having a diameter greater than a diameter of a body of the second elongated section that extends between the external threading and the stopping member;
   a movable element separate from the shaft, the movable element having a through-hole therein, the through-hole sized and configured to enable movement of the movable element along the body of the second elongated section of the shaft, wherein a length of the body of the second elongated section along which the movable element moves is adjusted by varying a depth by which the external threading at the second end of the second elongated section is engaged with the internal threading of the aperture in the second end of the first elongated section; and
   a locking mechanism configured to secure the movable element to the shaft, the locking mechanism includes:
      a locking bolt configured to engage a threaded hole extending through the movable element in a direction substantially perpendicular to a longitudinal axis of the shaft; and
      a locking hole formed in the shaft, the locking hole sized and configured to substantially align with the threaded hole such that the locking bolt is positioned to extend through the threaded hole into the locking hole.

2. The medical instrument of claim 1, wherein the hook has a circular, a rectangular, or a flat-plate configuration.

3. The medical instrument of claim 1, wherein the internal threading in the aperture in the second end of the first elongated section corresponds to the external threading on an external surface of the second end of the second elongated section to enable the second ends of the first and second elongated sections to be removably attached to each other.

4. The medical instrument of claim 3, wherein the shaft is adjustable in length by varying a depth at which the external threading is engaged with the internal threading.

5. The medical instrument of claim 1, wherein the stopping member comprises a first stopping member, and wherein the aperture is formed in a second stopping member of the second end of the first elongated section, the second stopping member being integral with the first elongated section and having a diameter greater than that of the through-hole in the movable element to confine the movable element between the first stopping member and the second stopping member along the shaft.

6. The medical instrument of claim 5, further comprising a spring positioned around the body of the second elongated section of the shaft between the second stopping member and the movable element.

7. The medical instrument of claim 6, wherein the spring is sized and configured to be compressed against the second stopping member at the second end of the first elongated section to enable the spring to generate a force on the movable element in a direction of the first stopping member.

8. The medical instrument of claim 1, wherein the movable element includes contours formed on an outer surface of the movable element.

9. The medical instrument of claim 1, wherein a cross-sectional shape of the through-hole and a cross-sectional shape of at least a portion of the second elongated section are non-circular.

* * * * *